United States Patent [19]

Adam et al.

[11] Patent Number: 5,318,440

[45] Date of Patent: Jun. 7, 1994

[54] FIBER REINFORCED ORTHODONTIC APPLIANCE AND METHOD OF MANUFACTURE

[75] Inventors: Randall E. Adam, Temple City; James D. Cleary, Glendora; Jerold S. Horn, Los Angeles; Said Pazirandeh, Glendora, all of Calif.

[73] Assignee: Minnesota Mining and Manufacturing Company, St. Paul, Minn.

[21] Appl. No.: 903,568

[22] Filed: Jun. 24, 1992

[51] Int. Cl.$^5$ ............................................. A61C 7/00
[52] U.S. Cl. ....................................................... 433/8
[58] Field of Search ................................. 433/8, 9, 10

[56] References Cited

U.S. PATENT DOCUMENTS

| | | | |
|---|---|---|---|
| 3,930,311 | 1/1976 | Andrews | 32/14 A |
| 3,955,282 | 5/1976 | McNall | 32/14 C |
| 3,964,165 | 6/1976 | Stahl | 433/8 |
| 4,186,488 | 2/1980 | Wallshein | 433/8 |
| 4,296,855 | 10/1981 | Blalock | 198/502 |
| 4,302,532 | 11/1981 | Wallshein | 433/8 |
| 4,381,918 | 5/1983 | Ehrnford | 433/199 |
| 4,532,275 | 7/1985 | Aito et al. | 523/468 |
| 4,585,414 | 4/1986 | Kottemann | 433/20 |
| 4,639,218 | 1/1987 | Jones et al. | 433/8 |
| 4,717,341 | 1/1988 | Goldberg et al. | 433/9 |
| 4,793,803 | 12/1988 | Martz | 433/6 |
| 4,793,809 | 12/1988 | Sigler et al. | 433/218 |
| 4,894,012 | 1/1990 | Goldberg et al. | 433/215 |
| 4,950,439 | 8/1990 | Smith et al. | 264/294 |
| 4,954,080 | 9/1990 | Kelly et al. | 433/8 |
| 4,961,700 | 10/1990 | Dunbar | 425/394 |
| 4,983,334 | 1/1991 | Adell | 264/16 |
| 4,988,293 | 1/1991 | Collins et al. | 433/8 |
| 5,023,041 | 6/1991 | Jones et al. | 264/510 |
| 5,064,439 | 11/1991 | Chang et al. | 623/66 |
| 5,078,596 | 1/1992 | Carberry et al. | 433/8 |

FOREIGN PATENT DOCUMENTS

| | | |
|---|---|---|
| 3831230 | 3/1990 | Fed. Rep. of Germany . |
| 58-167504 | 10/1983 | Japan . |
| 61-152607 | 7/1986 | Japan . |
| 61-218507 | 9/1986 | Japan . |
| WO91/11153 | 8/1991 | PCT Int'l Appl. . |
| 2253420 | 9/1992 | United Kingdom . |

OTHER PUBLICATIONS

"The use of continuous fiber reinforcement in dentistry", A. J. Goldberg, C. J. Burstone, *Dental Materials*, May 1992, pp. 197–202.

"Hydolytic Stability of Continuous Glass Fiber Reinforced Thermoplastics", A. J. Goldberg, C. J. Burstone and I. Hadjinikolaou, Abstract #1658, University of Connecticut Health Center.

"Design Limitations of Fiber-Reinforced Composite Intended for Dental Applications", I. Hadjinikolaou and A. J. Goldberg, Abstract #1366, University of Connecticut Health Center.

Promotional Material, entitled "Cosmetic Orthodontics", American Orthodontics, Sheboygan, Wisc. (undated).

Promotional Material, entitled "The Wedding of Rachel Williams and Dan Pelissier", American Orthodontics, Sheboygan, Wisc. (undated) (2 pages).

(List continued on next page.)

*Primary Examiner*—Paul J. Hirsch
*Attorney, Agent, or Firm*—Gary L. Griswold; Walter N. Kirn; James D. Christoff

[57] ABSTRACT

An orthodontic appliance such as a bracket is made of a polymeric material with reinforcing fiber structure embedded in the polymeric material. The reinforcing fiber structure includes relatively long filaments that extend about the perimeter of the bracket including the periphery of an archwire slot. In one embodiment, a method for making the bracket includes the steps of placing a tubular fiber preform in a mold assembly in an orientation aligned with a mesial-distal axis of the resultant bracket, and then closing the mold assembly in directions toward a central axis of the preform.

15 Claims, 4 Drawing Sheets

OTHER PUBLICATIONS

"Aramid Fiber Reinforcement of Acrylic Appliances", by Richard H. Mullarky, DDS, *Journal of Clinical Orthodontics*, vol. XIX, No. 9, pp. 655-658 (copyright 1985).

"The effect of carbon fiber orientation on the fatigue resistance and bending properties of two denture resins", J. DeBoer, DDS, S. G. Vermilyea, DMD, MS and R. E. Brady, DMD, *The Journal of Prosthetic Dentistry*, Jan. 1984, vol. 51, No. 1, pp. 119-121.

"Denture base acrylic reinforced with high modulus fibre", Grave AMH, Chandler HD, Wolfaardt JF, *Dent Mater* 1985:1:185-187.

"A Study on the Denture Base with Carbon Fiber Reinforced Hybrid Composite", Hiroshi Kimura et al., *J. Jap. Res. Soc. Dent. Mat. Appl.*, V. 33, pp. 297-305, 1976.

"A Study on the Reinforcement of Acrylic Denture Base", Hiroshi Kimura et al., *J. Jap. Res. Soc. Dent. Mat. Appl.*, V. 33, pp. 350-358, 1977.

"A Study on the Effects of the Carbon Fiber and Stainless Steel Reinforced P.M.M.A. for Lower Resin Denture", *J. Jap. Soc. Dent. Mat. Appl.*, V. 34, pp. 58-67, 1977.

"A Study on the Carbon Fiber Reinforced Denture Resin Base", Hiroshi Kimura et al., *J. Jap. Res. Soc. Dent. Mat. Appl.*, V. 34, pp. 116-125, 1977.

"A Study on the Self Adhesion of Carbon Fiber Prepreg and Dental Acrylic Resin on the Hybrid Composites of Thin Plate", Hiroshi Kimura et al., *J. Jap. Res. Soc. Dent. Mat. Appl.*, V. 34, pp. 168-177, 1977.

"A Study on the Self Adhesion of Carbon Fiber Prepreg and Dental Acrylic Resin on the Hybrid Composites of Thin Plate", Hiroshi Kimura et al., *Fukui Daigaku Kogakubu Kenkyo Hokoku*, 25(2), pp. 153-160.

"A Study on the Environmental Deterioration of Dental P.M.M.A. Bonded Parts", Hiroshi Kimura et al., *J. Jap. Res. Soc. Dent. Mat. Appl*, V. 36, pp. 102-111, 1979.

"A Study on the Fatigue Characteristics of Bonded Parts of the Carbon Fiber Reinforced Dental" P.M.M.A., Hiroshi Kimura et al., *J. Jap. Res. Soc. Dent. Mat. Appl.*, V. 36, pp. 202-208, 1979.

"A Study on the Fiber Orientation Effects of Carbon Fiber Reinforced Anisotropy Dental Polymer Hyubrid Composites on the Extreme Thin Plate", Hiroshi Kimura et al., *J. Jap. Res. Soc. Dent. at. Appl.*, V. 35, pp. 115-122, 1978.

"A Study on the Carbon Fiber Reinforced Dental P.M.M.A. Composites of Thin Plate with Brush on Technic Method", Hiroshi Kimura et al., *J. Jap. Res. Soc. Dent. Mat. Appl.*, V. 35, pp. 123-129, 1978.

Abstract of Japanese Application No. 59-161307.

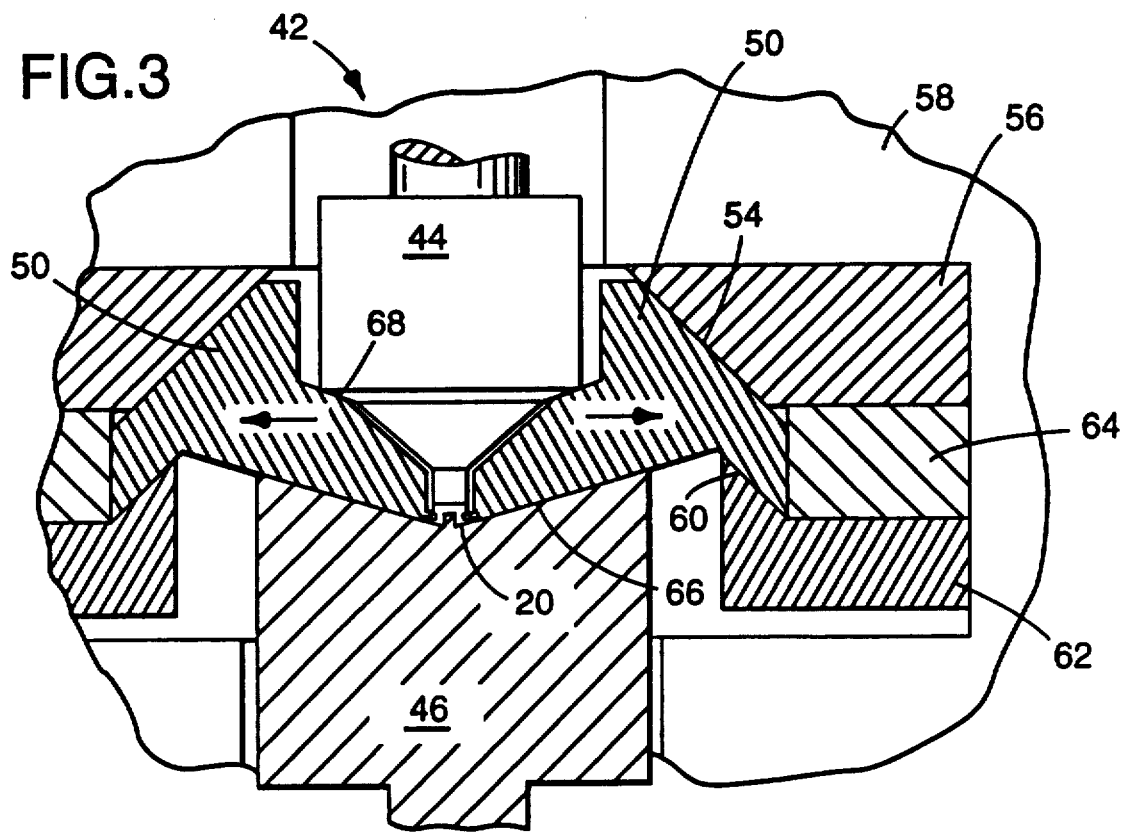
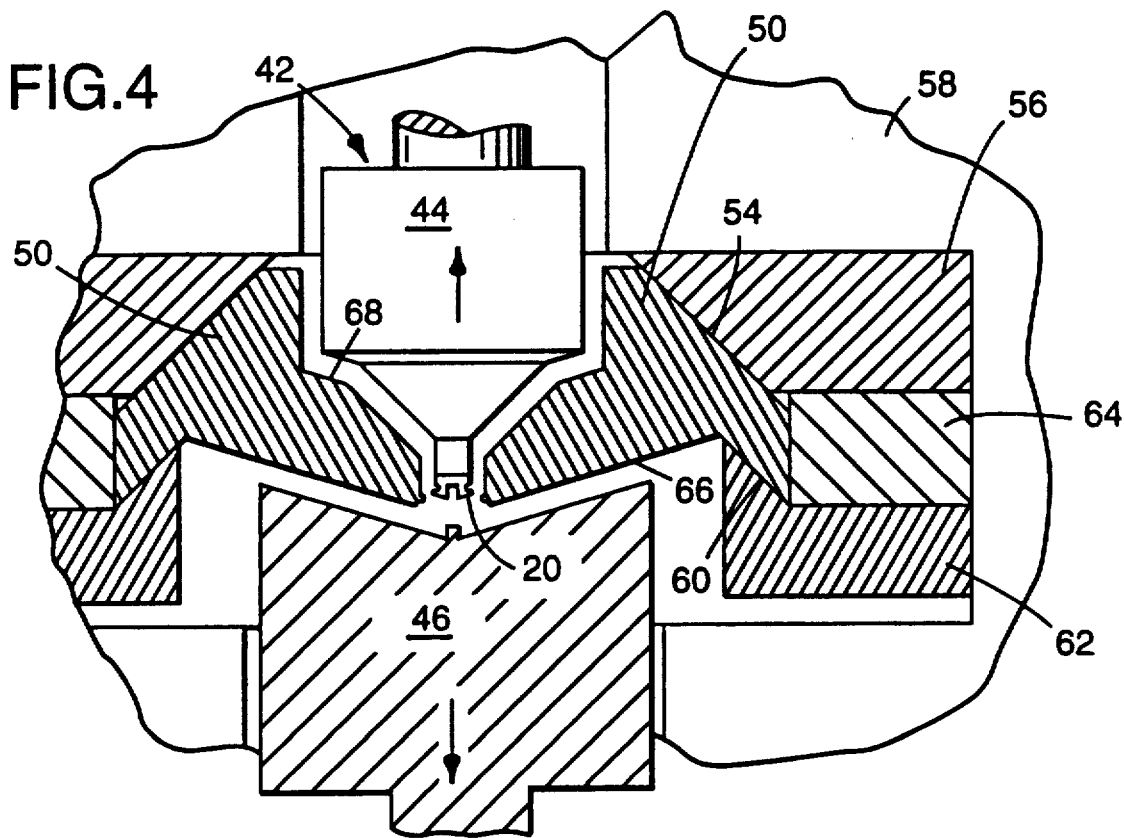

FIBER REINFORCED ORTHODONTIC APPLIANCE AND METHOD OF MANUFACTURE

BACKGROUND OF THE INVENTION

1. Field of the Invention

This invention relates to an orthodontic appliance and a method for manufacturing an orthodontic appliance that is made of polymeric material and reinforcing fiber embedded in the polymeric material.

2. Description of the Related Art

Orthodontic treatment concerns movement of improperly aligned or malpositioned teeth to desired orientations. Orthodontic treatment often involves the use of small appliances known as brackets that are secured to incisor, bicuspid and cuspid teeth, and buccal tubes that are secured to molar teeth. The brackets and buccal tubes have small slots or passages that receive a resilient, metallic archwire. The archwire forms a track to guide movement of the teeth, and the teeth are urged toward desired positions by bends or twists placed in the archwire, or by the use of other devices such as elastomeric modules.

Many brackets and buccal tubes have been made of stainless steel because stainless steel is strong, non-absorbent, weldable and relatively easy to form and machine. However, adults and older children undergoing orthodontic treatment are sometimes embarrassed by the "metallic smile" appearance of such brackets. Further, certain patients are allergic to nickel and chromium that are often present in stainless steel appliances.

Orthodontic appliances are sometimes made of materials other than alloys containing nickel and chromium and can be used for patients sensitive to these elements. For example, orthodontic appliances may be made of a ceramic such as monocrystalline or polycrystalline alumina. U.S. Pat. No. 4,954,080 describes orthodontic appliances made of a polycrystalline ceramic having a translucency which minimizes visibility of the appliance when mounted on a tooth so that the problem of a "metallic smile" is largely avoided.

However, ceramic brackets are known to present a greater resistance to movement of the bracket relative to the archwire as compared to metal brackets. Resistance to movement is considered a disadvantage because the resistance slows movement of the teeth to positions desired by the orthodontist and can lengthen treatment time.

Orthodontic appliances have also been made of a plastic material that in some instances is translucent and neutral in color. Preferably, the selected plastic material is relatively resistant to staining by food and beverages such as mustard, spaghetti sauce and grape juice. It is also desired that the plastic material be relatively resistant to creep so that the sides of the archwire slot do not unduly deform.

Attempts have also been made to strengthen plastic orthodontic appliances by use of reinforcing fibers or whiskers. For example, plastic brackets containing fibers were promoted by American Orthodontics of Sheboygan, Wisconsin as early as 1985. U.S. Pat. No. 5,078,596 discloses an orthodontic bracket made of polycarbonate and translucent glass or ceramic fibers. It has been suggested that brackets may be made by injecting both resin and chopped fibers into a mold assembly.

U.S. Pat. No. 4,717,341 describes an orthodontic bracket produced from glass-filled polycarbonate composite material by injection into a heated aluminum mold. An opening to the mold is placed in the base directly under the center of the slot apparently in an attempt to achieve a certain orientation of the fibers.

There is a continuing interest in making orthodontic appliances as small as practicable so that for aesthetic reasons the visibility of the appliance is reduced. However, it is important that the appliance have sufficient strength to resist breakage during ordinary use. Orthodontic appliances are often subject to significant stress during mastication when the bracket may contact hard food portions, occluding teeth or appliances mounted on occluding teeth.

In addition, certain smaller sections of appliances need to withstand relatively strong forces that may be intentionally induced during orthodontic treatment. For example, brackets often have tiny tiewings shaped like hooks on opposite sides of the archwire slot for receiving a wire or elastic ligature that is used to bind the archwire to the bracket. Such tiewings, if weak, may break apart from the body of the bracket when an attempt is made to firmly seat the archwire in the bottom of the slot. As can be understood, replacement of fractured brackets is a nuisance for both the orthodontist and patient.

There is a continuing need in the art for a plastic orthodontic appliance that is relatively small and yet has sufficient strength and stiffness, particularly in regions of the tiewings and sections near the archwire slot. Preferably, such a bracket would be made according to a method that is relatively inexpensive, adaptable for automation and yet provides consistent, satisfactory results.

SUMMARY OF THE INVENTION

The present invention is directed toward an orthodontic appliance that comprises a body having an elongated archwire slot and a mesial-distal reference axis. The archwire slot has a certain periphery in reference planes generally perpendicular to the mesial-distal reference axis. The body is made of a polymeric material and reinforcing fiber structure embedded in the polymeric material. The reinforcing fiber structure includes at least one filament and comprises at least one layer. The at least one layer includes a number of aligned, side-by-side stretches of the at least one filament that lie in the reference planes and extend about a majority of the periphery of the archwire slot.

The orthodontic appliance in accordance with the invention has relatively long fibers that provide the appliance with significant strength in narrow sections that may be subject to relatively high stress. For example, an orthodontic bracket of the invention has significant stiffness and resistance to fracture in narrow sections of the bracket between the archwire slot and the tiewing undercuts and also in sections between the bottom of the slot and the base. Alignment of adjacent filament stretches in an orientation perpendicular to the mesial-distal reference axis enables the bracket body to satisfactorily withstand torquing forces that may be imposed by an archwire in the slot. The long, oriented fibers enable the appliance to be made with relatively high ratios of fiber to resin and selected anisotropic characteristics so that the resultant appliance exhibits satisfactory modulus of elasticity, sheer strength and creep properties in comparison to appliances made with shorter fibers.

The invention also concerns a method for making an orthodontic appliance. The method includes the steps of forming a fiber preform having a central axis. A quantity of polymeric material and the fiber preform are placed in a cavity of a mold assembly in a position wherein the central axis of the preform is generally parallel to an axis of the mold cavity that corresponds to a mesial-distal axis of the resultant appliance. The mold assembly is closed in directions generally toward the central axis of the preform.

A method for making an orthodontic appliance according to another embodiment of the invention comprises the steps of forming a fiber preform having a central axis with an overall length at least generally equivalent to the mesial-distal length of the resultant appliance. A quantity of polymeric material and the fiber preform are placed in a cavity of a mold assembly in a position wherein the central axis of the preform is generally parallel to an axis of the cavity that corresponds to a mesial-distal axis of the resultant appliance. At least one filament of the preform is caused to move along a reference plane generally perpendicular to the central axis and toward an orientation at least partially about a lateral periphery of an archwire slot of the appliance as the mold assembly is closed.

DETAILED DESCRIPTION OF THE DRAWINGS

FIG. 3 is a view somewhat similar to FIG. 2 except that the mold assembly is shown in a partially retracted orientation;

FIG. 4 is a view somewhat similar to FIG. 3 except that the mold assembly is shown in a fully retracted orientation;

DETAILED DESCRIPTION OF THE PREFERRED EMBODIMENTS

Figure 8:
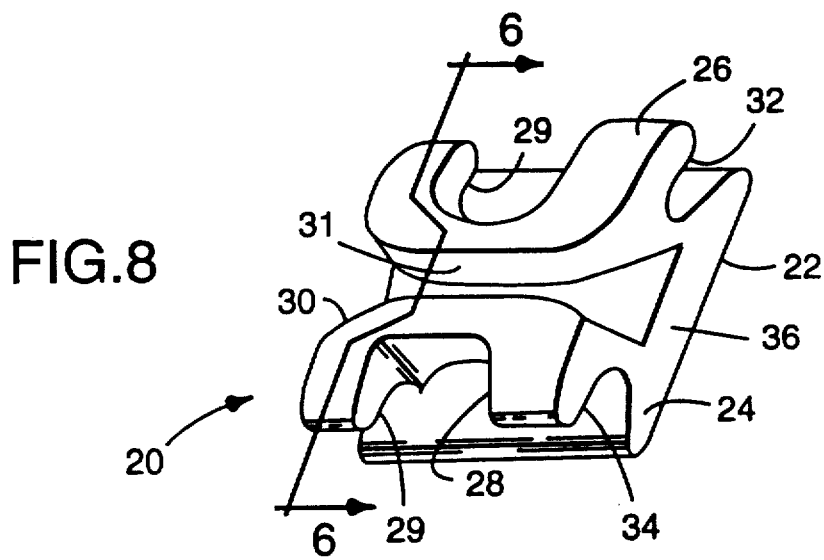
FIG. 8 is an enlarged perspective view of an appliance made with the preform of FIG. 7.

An orthodontic appliance 20 according to one embodiment of the invention is a bracket as shown in FIG. 8 and includes a tooth-facing base 22 having a compound contour to match the contour of the underlying tooth surface. The base 22 is connected to a central body 24 that, in turn, is connected to an occlusal tiewing 26 and a gingival tiewing 28. The tiewings 26, 28 have mesial and distal portions partially separated by a notch 29. Alternatively, mesial and distal portions could be fully separated from one another as in the case of a "twin" bracket.

The tiewings 26, 28 are spaced from each other by an elongated archwire slot 30 having a central portion 31 with a rectangular, generally U-shaped periphery when observed in directions perpendicular to a mesial-distal reference axis of the appliance (that, for some brackets, is co-linear with the longitudinal axis of the slot 30). The central portion 31 of the slot 30 has a width and depth closely complemental to the dimensions of an archwire having a rectangular cross-sectional configuration. An occlusal tiewing undercut 32 lies between the base 22 and an occlusal edge of the mesial and distal portions of the occlusal tiewing 26, and a gingival tiewing undercut 34 lies between the base 22 and a gingival edge of the mesial and distal portions of the gingival tiewing 28. The undercuts 32, 34 are in the nature of elongated grooves.

The appliance 20 has a mesial side 36 and a distal side that is not shown in the drawings but is on a side of the appliance opposite the mesial side 36. The undercuts 32, 34 and the archwire slot 30 extend across the appliance 20 from the mesial side 36 to the opposite, distal side in a direction parallel to the mesial-distal axis of the appliance 20. As an alternative, the archwire slot of brackets for certain teeth is inclined in occlusal-gingival directions relative to both the mesial-distal axis and the tiewing undercuts to provide an orthodontic preadjustment known as anqulation.

The appliance 20 is made of polymeric material and a length of reinforcing fiber structure embedded in the polymeric material. The reinforcing fiber structure has at least one layer that includes a number of side-by-side stretches of one or more filaments that extend in aligned relation in reference planes generally perpendicular to the mesial-distal axis of the appliance 20. Preferably, the aligned stretches extend about a majority of the extent of the U-shaped cross-sectional periphery of the archwire slot 30, and more preferably about the entire extent of the perimeter of the body 24 in such reference planes including the slot periphery, so that continuous stretches of the filaments extend across sections of the appliance 20 that are typically relatively narrow.

Figure 7:
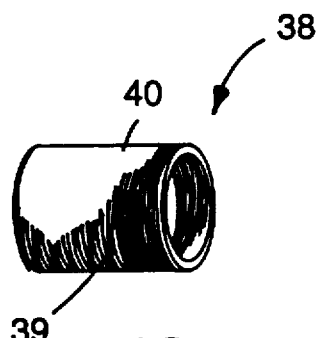
FIG. 7 is an enlarged perspective view of the preform shown in FIG. 5.

One satisfactory reinforcing fiber structure is a preform 38 as shown in FIG. 7 that is initially hollow and cylindrical. The preform 38 is made by winding a multi-strand fiber or tow 39 having a number of long, continuous filaments 40 about the central axis of a bobbin in a helical, tightly coiled, multiple-layer fashion with adjacent stretches of the tow 39 in the same radial plane or layer being in side-to-side contact with one another. As an alternative, adjacent stretches of the tow 39 in the same radial plane could lie spaced apart from one another. Preferably, the layers lie in face-to-face, tightly overlapped relation to one another. Optionally, some portions of the tow 39 extend in a direction parallel or generally parallel to the central axis of the preform 38.

As another alternative, the preform may be a woven fabric having filaments extending in cross directions. The fabric may initially have a multi-layered coiled configuration or a single layer, U-shaped configuration such that some of the filaments in the resultant appliance extend in planes perpendicular to its mesial-distal axis, while other filaments extend in directions parallel to its mesial-distal axis.

The filaments 40 are preferably made of a transparent or translucent material such as glass, ceramic or quartz. Preferably, the polymeric material is also transparent or translucent, and the index of refraction of the filaments 40 is approximately equal to the index of refraction of the polymeric material so that light entering the labial surface of the appliance 20 is transmitted through the appliance 20, reflected off of the surface of the tooth and then retransmitted through the appliance 20 toward its labial surface. In this manner, the appliance 20 takes on the color of the underlying tooth and blends with adjacent tooth structure.

The polymeric material is a thermoset or thermoplastic material that has sufficient strength to resist undue creep, deformation or fracture. Preferably, the polymeric material is relatively resistant to staining by food and beverages such as mustard, spaghetti sauce and grape juice.

Suitable thermoset resins include epoxies (such as TACTIX brand epoxy (no. 123/H41, Dow Chemical) and EPON brand resin (Shell Chemical)), acrylics, polyesters, polyurethanes and mixtures thereof. Suitable acrylics include diglycidyl-methacrylate of bisphenol A ("Bis-GMA"), triethyleneglycol dimethacrylate ("TEGDMA"), polyethyleneglycol dimethacrylate 600 ("PEGDMA 600"), urethane dimethacrylate, and trimethylolpropane triacrylate. A presently preferred thermosetting resin is a 30:36:33 mixture by weight of Bis-GMA, TEGDMA and PEGDMA 600 respectively.

Suitable thermoplastic resins include acrylics (such as nos. NAS 30, NAS 50 or ZYLAR 90, Novacor, or no. XT250, CYRO Industries). Other suitable thermoplastic resins include polysulfones (such as UDEL brand polysulfone, Amoco), polycarbonates (such as LEXAN brand polycarbonate, GE) polyesters or polyurethanes. A presently preferred thermoplastic resin is NAS 50.

Preferably, the filaments 40 are fully wetted by the polymeric material before the latter is shaped (and cured, if the material is a thermosetting material) in order to enhance the strength and translucency of the resulting appliance 20. The filaments 40 are preferably fully wetted before winding into the shape of the preform 38. In general, if the polymeric material is a liquid, the filaments 40 are wetted by dipping the tow 39 in a tray of the liquid. Once shaped to a cylinder, the wetted preform 38 is fixated by partial curing or by freezing to increase the viscosity of the polymeric material and facilitate handling of the preform 38. If the polymeric material is a thermoplastic, the tow 39 is electrostatically coated with the thermoplastic powder and then heated in an oven to melt the powder. Final shaping (and curing, if the material is a thermosetting material) of the impregnated preform 38 occurs during molding.

A mold assembly 42 is shown in FIGS. 1-6 and includes a plunger 44 and a clamp 46, both of which are movable in vertical directions viewing the drawings. Although not shown, the plunger 44 and the clamp 46 are each connected to a respective double-acting hydraulic piston and cylinder assembly. A controller that includes a mini-computer is connected to each piston and cylinder assembly in order to enable independent, timed movement of the plunger 44 and the clamp 46 in the sequence described below.

Figure 5:
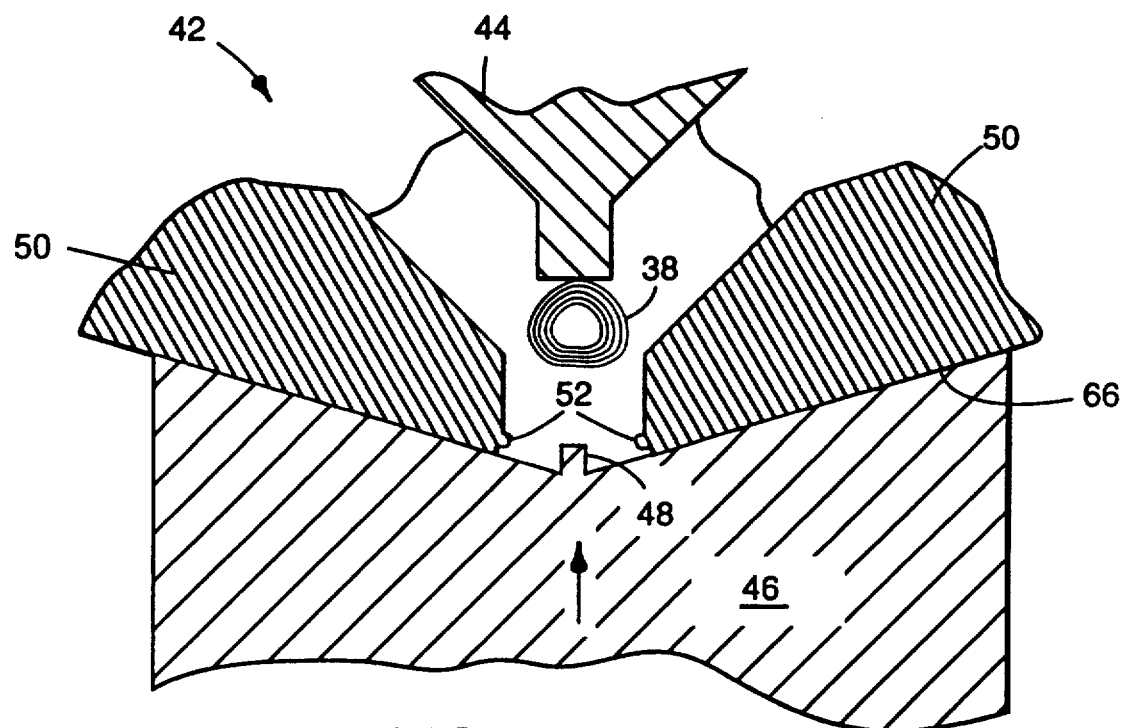
FIG. 5 is an enlarged, fragmentary, side cross-sectional view of the preform and mold assembly shown in FIG. 1.
Figure 6:
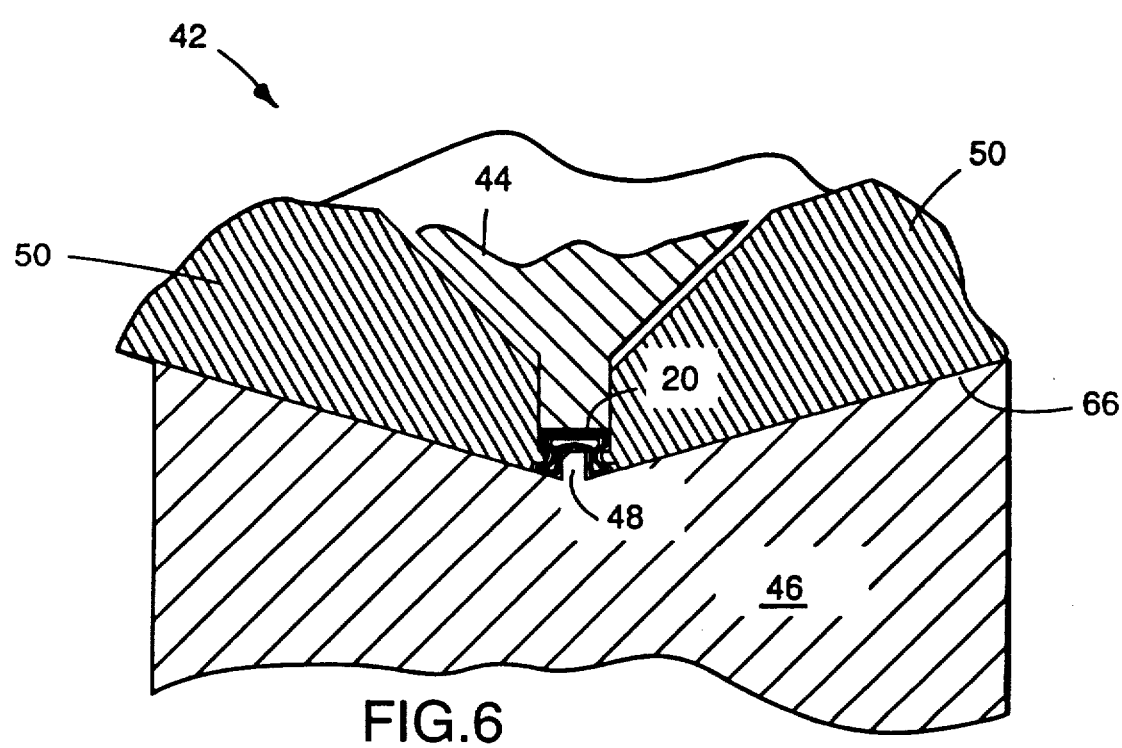
FIG. 6 is an enlarged, fragmentary, side cross-sectional view of the mold assembly and appliance shown in FIG. 2, wherein the appliance is taken along lines 6—6 of FIG. 8; and cross-hatching of the appliance has been deleted for clarity

As shown in more detail in FIGS. 5 and 6, a central portion of the clamp 46 includes an upstanding projection 48 that is of a size and orientation to form the archwire slot 30 in the resultant appliance 20. Sections of the clamp 46 adjacent the projection 48 are concave and form smoothly curved labial surfaces of the tiewings 26, 28.

The plunger 44 includes a central, depending section having a lowermost convex surface with a compound contour in order to form a contour on the base 22 that matches the curvature of the tooth. The lowermost surface of the plunger 44 is preferably scored, knurled or grooved so that the resultant base 22 has surface structure for controlling or facilitating movement of the adhesive used to bond the appliance 20 to a tooth as the appliance 20 is pressed toward the surface of the tooth.

The mold assembly 42 also includes four slides 50 for molding the occlusal, mesial, distal and gingival sides of the appliance 20. The two slides 50 that are shown in the drawings form the occlusal and gingival sides, and each include a protrusion 52 for shaping the tiewing undercuts 32, 34 respectively as illustrated in more detail in FIGS. 5 and 6. Surfaces of the slides 50 next to the protrusions 52 are curved to provide a smooth contour for remaining occlusal and gingival surfaces of the appliance 20 from the base 22 to the labial surfaces of the tiewings 26, 28.

An upwardly-facing, outer inclined surface 54 of each of the four slides 50 is in sliding contact with an inner, downwardly-facing inclined surface of a clamp ring 56 that is secured in a cavity of a load frame 58. An outer, inclined, downwardly-facing surface 60 of each slide 50 is in sliding contact with an upwardly-facing, inclined surface of a cam ring 62 that is also secured within the cavity of the load frame 58. A spacer 64 lies between the cam ring 62 and the clamp ring 56.

An inner, downwardly-facing, inclined surface 66 of each slide 50 is slidingly engageable with an upwardly-facing, inclined surface of the clamp 46. Additionally, an inner, upwardly-facing, inclined surface 68 of each slide 50 is slidingly engageable with an inclined, downwardly-facing surface of the plunger 44. The two slides 50 shown in the drawings are movable in a generally horizontal direction in the plane of the drawings, while the two remaining slides 50 not shown in the drawings are movable in a generally horizontal direction perpendicular to the plane of the drawings.

Figure 1:
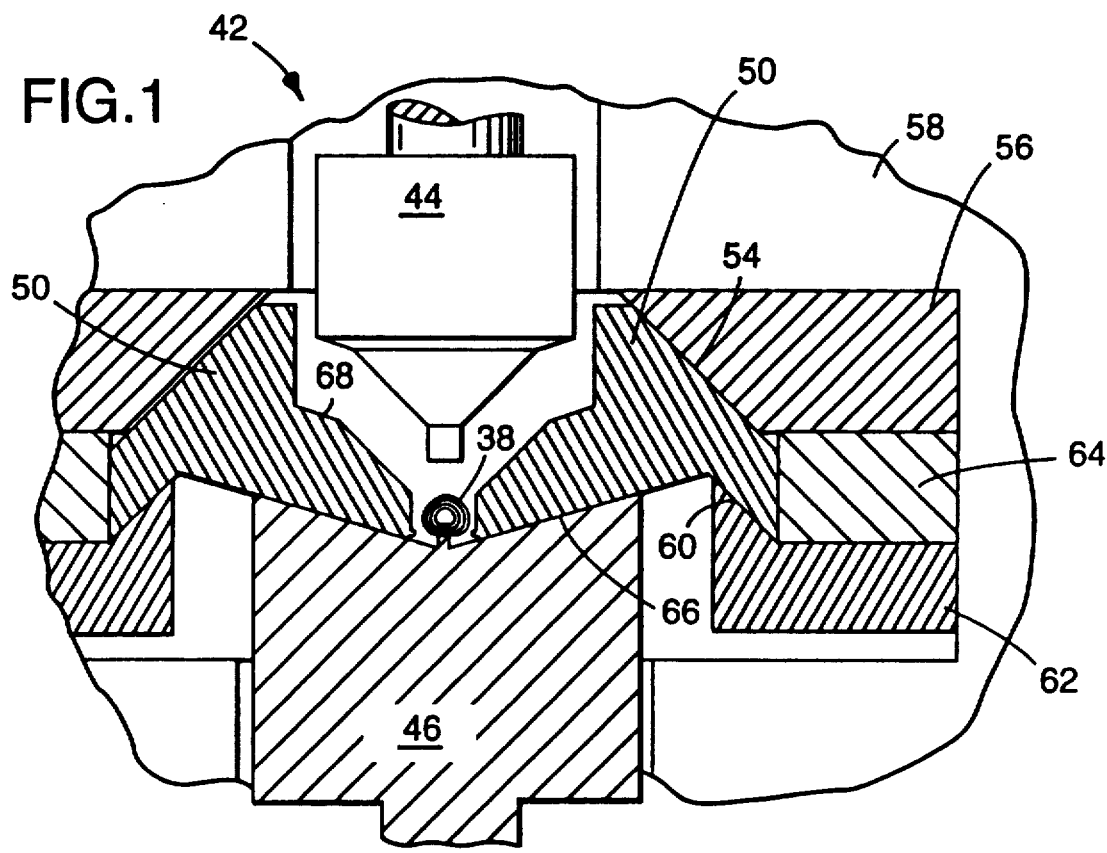
FIG. 1 is a side cross-sectional view of a preform and mold assembly for making an orthodontic appliance in accordance with the invention, showing the mold assembly in an initial orientation.

In operation, the preform 38 is introduced into the mold cavity of the mold assembly 42 in the orientation depicted in FIGS. 1 and 5 wherein the preform 38 lies atop the projection 48 and substantially parallel with the longitudinal axis of the protrusions 52 for forming the tiewing undercuts 32, 34. The preform 38 is introduced into the mold cavity through a feed tube that leads from a bobbin winder assembly for winding the tow 39 into the preform 38. Preferably, the bobbin winder assembly is associated with several feed tubes that direct the preforms to a number of mold assemblies in turn.

Next, the clamp 46 is held in a stationary position while the plunger 44 is moved downwardly toward the clamp 46 to flatten the preform 38 against the projection 48 and cause occlusal and gingival portions of the preform 38 to drape over the projection 48. Subsequently, the plunger 44 is lifted while the clamp 46 is raised. As the clamp 46 ascends, sliding contact of surfaces 66 of the slides 50 against the clamp 46 and sliding contact of the surfaces 54 against the clamp ring 56 urge the slides 50 to move into the mold cavity toward one another and toward the preform 38. The clamp 46 is raised a distance sufficient to move the four slides 50 inwardly to desired positions for molding the mesial, distal, occlusal and gingival sides of the resultant appliance 20 including the tiewing undercuts 32, 34.

Figure 2:
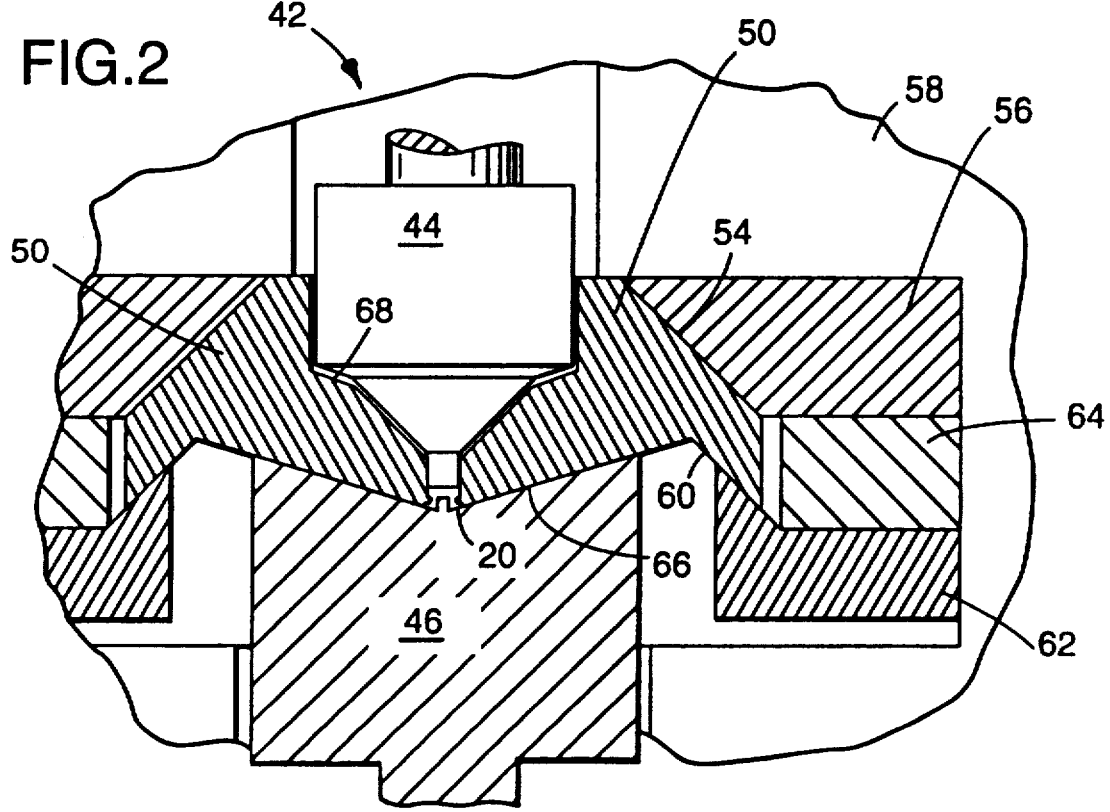
FIG. 2 is a view somewhat similar to FIG. 1 except that the mold assembly is shown in a closed orientation to form the appliance (that is shown in section along lines 6—6 of FIG. 8)

Next, the plunger 44 is lowered while the clamp 46 is held in a stationary orientation to close the mold cavity of the mold assembly 42 as shown in FIG. 2 and to press the impregnated preform 38 to its final form matching the configuration of the desired appliance 20. To cure the polymeric material, heat is introduced into the mold cavity by electric resistance heaters embedded in the clamp 46 near the projection 48 or by an induction coil surrounding the clamp 46. If the material is thermoplastic, the mold assembly is heated before closing and cooled before opening; for a thermoset material, the assembly is closed before heating.

As the mold assembly 42 is closed, the shape of the preform 38 is changed from its initially cylindrical shape (FIG. 5) to the shape shown in FIG. 6 where the tow 39 including the filaments 40 extends around the perimeter of the appliance 20 in sections taken perpendicular to the mesial-distal axis of the appliance 20. More particularly, closing of the mold assembly 42 causes the tow 39 to be draped over the projection 48 such that the tow 39 ultimately extends around the archwire slot 30 in a direction transverse to the length of the archwire slot 30, along the labial portions of the tiewings 26, 28, around the curved surfaces of the tiewing undercuts 32, 34 and along the curved surface of the base 22. The resultant configuration of the preform 38 causes the density of the filament 40 (i.e., the weight ratio of the filaments 40 to the polymeric material) to be greatest in narrow sections of the bracket, namely in the relatively thin sections between the archwire slot 30 and the undercuts 32, 34, and in the section between the archwire slot 30 and the base 22.

Preferably, the outer circumference of the impregnated preform 38 is approximately equal to the perimeter of the appliance 20 (including all surfaces of the archwire slot 30 and the undercuts 32, 34 facing the atmosphere) in sections transverse to the mesial-distal axis of the appliance 20 so that when the preform 38 is collapsed and compressed in the mold assembly 42 the outer windings of the tow 39 are closely adjacent external surfaces of the appliance 20. Additionally, the inner diameter of the impregnated preform 38 is selected such that the initial volume of the impregnated preform 38, ignoring the volume of its hollow interior, is only slightly greater than the volume of the resultant appliance 20. As a result, when the mold assembly 42 is closed, the appliance 20 is formed without voids or spaces, and yet without excessive amounts of polymer or fiber material that might otherwise unduly hinder closure of the mold assembly 42. As an example, a hollow preform for making a bracket somewhat similar to appliance 20 but having a uniform cross-section across its mesial-distal extent identical to the cross-section shown in FIG. 6 (i.e., lacking notches 29 and cut-away archwire relief areas next to its mesial and distal sides) has an outer diameter of 3.9 mm, an inner diameter of 3.2 mm and an overall length of 3.6 mm.

When the mold assembly 42 is in its closed position as shown in FIGS. 2 and 6, excess polymer material is urged upwardly along small external channels formed in the plunger 44 to a small undercut region that serves as an overflow reservoir. As the polymer material in the mold cavity is cured, the polymer material in the channels and the overflow reservoir is also cured and thereafter functions as a handle for retaining the molded appliance 20 on the plunger 44 during opening of the mold assembly 42.

An initial stage of opening the mold assembly 42 is shown in FIG. 3 and is carried out by shifting the plunger 44 downwardly while releasing pressure in the hydraulic cylinder connected to the clamp 46 so that the clamp 46 is no longer stationary and is somewhat free to descend. As the plunger 44 is urged downwardly, the plunger 44 slides against the surfaces 68 of the slides 50, urging the surfaces 60 to slide against the cam ring 62 and thereby cause the slides 50 to move outwardly and away from the mold cavity until the protrusions 52 clear respective occlusal and gingival sides of the appliance 20.

Next, the piston and cylinder assemblies are pressurized to move the plunger 44 upwardly and the clamp 46 downwardly until the mold assembly 42 is in its retracted or open orientation as illustrated in FIG. 4. The plunger 44 is then raised a distance sufficient to position the appliance 20 above the load frame 58.

Next, a trough (not shown) is moved to a location beneath the appliance 20 and a pin (also not shown) is moved to eject the appliance 20 from the bottom of the plunger 44. The pin is located within the central, lower portion of the plunger 44 and, when moved toward a lowermost, extended position, is operable to sever the appliance 20 from the cured excess polymer material forced from the mold cavity and into the channels and overflow reservoir. The above sequence of operation of the mold assembly 42 is then repeated to make additional appliances as desired.

Figure 9:
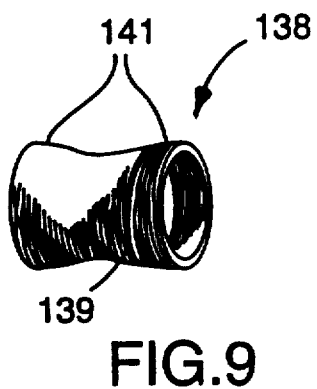
FIG. 9 is an enlarged perspective view of a preform in accordance with another embodiment of the invention.

A preform 138 in accordance with another embodiment of the invention is shown in FIG. 9 and comprises a central core of a wound tow 139 that extends substantially along the entire mesial-distal extent of the resultant appliance. Additional windings of the tow 139 are provided at mesial and distal sides of the central core as shown at 141. The additional windings at the locations 141 facilitate complete filling of the mold cavity or appliances having additional volume in mesial and distal regions (e.g., in instances such as "twin" brackets having mesial and distal tiewings completely spaced apart from each other, where additional resin and fiber are desired on mesial and distal regions).

Figure 10:
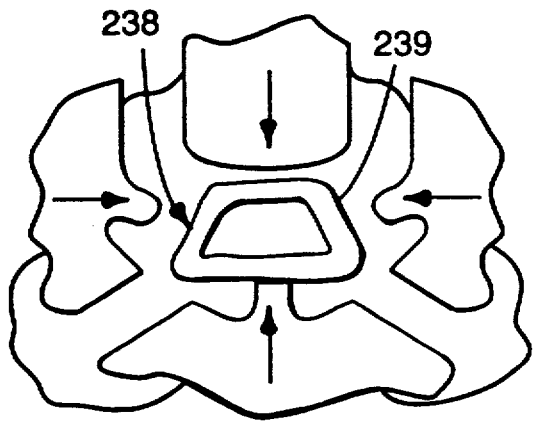
FIG. 10 is a schematic view somewhat similar to FIG. 5 but showing a preform in accordance with yet another embodiment of the invention.

A preferred preform 238 is illustrated in FIG. 10 and has a generally trapezoidal configuration in sections perpendicular to its mesial-distal axis. The trapezoidal shape is advantageous for facilitating lateral movement of the preform 238 to the desired cross-sectional configuration of a bracket as the mold assembly 42 is closed. Viewing FIG. 10, the lower, outermost corners of the preform 238 provide enhanced flow of the tow 239 and polymer material into tiewing portions of the molded appliance.

Figure 11:
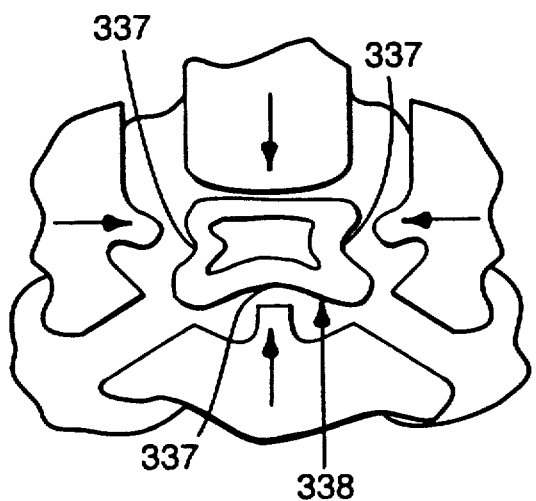
FIG. 11 is a schematic view somewhat similar to FIG. 5 but showing a preform in accordance with a further embodiment of the invention.

An alternative preform 338 is shown in FIG. 11 The preform 338 is made by altering the trapezoidal configuration of the preform 238 shown in FIG. 10 by placing the preform 238 in a mechanism (not shown) having arms that form indentations 337 into sides corresponding to occlusal, gingival and labial surfaces of the resultant appliance. The preform 338 is partially fixated in the mechanism in order to facilitate subsequent handling so that the preform 338 will substantially retain its shape until in the mold cavity.

The following paragraphs describing preparation of test articles and also an example according to the invention should not be construed as limiting the scope of the invention. Unless otherwise indicated, all parts and percentages are on a weight basis.

PREPARATION OF TEST ARTICLES

A thermosetting resin mixture was prepared by adding one part dicumyl peroxide catalyst (Luperox 500R, ATOCHEM) to 100 parts of a 30:36:33 mixture of BisGMA, TEGDMA and PEGDMA 600. (no. 252, Sartomer)

Glass fiber tow (no. S-2 449-1250, Dow Corning) was cut into 10 cm segments and the segments were laid in a side-by-side single layer arrangement in a tray containing the resin mixture. The tray was part of a stop mold assembly having a rectangular cavity of 10 cm × 10 cm and was coated with a fluorocarbon mold release agent prior to use. The resin mixture was added to the tray, and the tow segments were allowed to soak for 90 minutes in the resin mixture while degassed in a bell jar.

The mold was partially closed and excess resin was squeezed from the tray by gravity pressure of the top mold segment. The partially closed mold assembly was further degassed in a bell jar for 30 minutes, and then placed in a press with sufficient pressure to complete closure of the mold. The mold was heated by press platens at 90° C. for 16 hours, then at 120° C. for 2 hours. The heat source was then deactivated and the mold allowed to cool to a temperature below 70° C. and then opened.

The cured fiber reinforced material was visually observed under a microscope and found to be translucent. Data from physical testing of the material showed a flexural yield strength of 370±10 MPa and a flexural modulus of 12410±660 MPa, satisfactory for orthodontic appliances.

Other test articles were made using a thermoplastic acrylic resin (NAS 50, Novacor) that was ground into a powder having an average particle size of 70 microns. The resin powder was coated on a glass fiber tow (no. S-2 449-1250, Dow Corning) by Electrostatic Technology, Inc. using powder coating technology such that the resultant tow had a resin to fiber ratio of 70:30.

The coated glass fiber tow was cut into 10 cm segments and the segments were laid in a side-by-side arrangement in multiple layers in the tray of the rectangular cavity stop mold assembly described above. The mold assembly was partially closed and placed between two press platens that had been preheated to 200° C. The platens were moved to contact the mold assembly and the temperature was monitored by a thermocouple attached to the mold assembly. The mold assembly reached 175° C. in about 15 minutes. At this time, the platens were pressed against the mold assembly with sufficient force to obtain closure of the mold, and the heat source was then deactivated. Once the mold assembly cooled to a temperature below 70° C., the assembly was opened.

The molded sheet was observed to be translucent. Data from physical testing of the sheet showed that the material exhibited a flexural yield strength of 480±20 MPa and a flexural modulus of 15170±280 MPa, satisfactory for orthodontic appliances.

EXAMPLE

A 10 cm length of the coated glass fiber tow mentioned above having a thermoplastic resin to fiber ratio of 70:30 was tightly wound around a mandrel that had been previously coated with a fluorocarbon release agent. A blower having a heater was directed at the tow during winding, and was subsequently deactivated to enable the wound preform to cool and retain its shape.

A mold assembly was provided for making an elongated integral bar of multiple bracket bodies that could be cut apart to produce individual brackets. The mold assembly included a stationary bottom wall for molding a base of the bracket bodies, and a top, vertically movable plunger for forming an archwire slot. Two slides, movable along the base in a generally horizontal direction, provided tiewing undercuts when urged in a direction toward the preform.

The impregnated, shaped preform was removed from the mandrel. The coiled preform was then cut to a length of about 2.5 cm and placed in the mold assembly with its longitudinal axis in a direction parallel with the overlying mold structure for forming the archwire slot and aligned with elongated protrusions on the slides for forming the tiewing undercuts. The mold assembly was partially closed, placed in the press having its platens preheated to 175° C. and the platens were moved to contact the mold assembly. The mold assembly reached 175° C. in 10 minutes, after which the platens were moved to fully close the mold. The heat source was then deactivated, the platen allowed to cool to 100° C. and the mold assembly was opened.

The molded bar was visually inspected under a microscope, and it was observed that the glass fibers extended along a path next to substantially the entire perimeter of the bar, including surfaces representing the base, tiewings and tiewing undercuts. The bar was also visually observed to be translucent.

We claim:

1. An orthodontic appliance comprising a body having an elongated archwire slot and a mesial-distal reference axis, said archwire slot having a certain generally U-shaped periphery in reference planes generally perpendicular to said mesial-distal reference axis, said body being made of polymeric material and reinforcing fiber structure embedded in said polymeric material, said reinforcing fiber structure including at least one filament and comprising at least on layer, said at least one layer including a number of aligned, side-by-side stretches of said at least one filament that lie in said reference planes and extend in a non-straight path about a majority of said generally U-shaped periphery of said archwire slot.

2. The appliance of claim 1, wherein said body in said reference planes has a perimeter that includes said periphery, and wherein said stretches extend in said reference planes about at least a majority of the extent of said perimeter.

3. The appliance of claim 2, wherein said stretches extend in said reference planes about substantially the entire extent of said perimeter.

4. The appliance of claim 1, wherein said at least one layer is wound about said mesial-distal reference axis.

5. The appliance of claim 1, wherein adjacent stretches of said at least one filament are in side-by-side arrangement in close proximity with each other.

6. The appliance of claim 1, wherein said stretches extend in said reference planes substantially about the entire extent of said archwire slot.

7. The appliance of claim 1, wherein said reinforcing fiber structure comprises a fiber tow having a number of filaments.

8. The appliance of claim 1, wherein said polymeric material is an acrylic.

9. The appliance of claim 1, wherein said polymeric material is a thermoset polymer.

10. The appliance of claim 1, wherein said polymeric material is a thermoplastic material.

11. The appliance of claim 1, wherein said polymeric material is a mixture of Bis-GMA, TEGDMA and PEGDMA.

12. The appliance of claim 1, wherein said reinforcing fiber structure has an index of refraction approximately equal to the index of refraction of said polymeric material.

13. An orthodontic appliance comprising a body having an elongated archwire slot and a mesial-distal reference axis, said archwire slot having a certain generally U-shaped periphery in reference planes generally perpendicular to said mesial-distal reference axis, said body being made of polymeric material and reinforcing fiber structure embedded in said polymeric material, said reinforcing fiber structure including a number of side-by-side stretches of one or more filaments that extend in a non-straight path about a majority of said generally U-shaped periphery of said archwire slot.

14. The appliance of claim 13, wherein said side-by-side stretches lie side-by-side in a mesial-distal direction.

15. The appliance of claim 13, wherein said side-by-side stretches lie side-by-side in an occlusal-gingival direction.

* * * * *

UNITED STATES PATENT AND TRADEMARK OFFICE
CERTIFICATE OF CORRECTION

PATENT NO. : 5,318,440

DATED : June 7, 1994

INVENTOR(S) : Randall E. Adam, James D. Cleary, Jerold S. Horn and Said Pazirandeh It is certified that error appears in the above-indentified patent and that said Letters Patent is hereby corrected as shown below:

Col. 4, line 36, "anqulation" should read -- angulation --.

Col. 8, line 43, "or" should read -- for --.

Col. 10, line 49, "on" should read -- one --.

Signed and Sealed this

Twenty-fourth Day of January, 1995

Attest:

BRUCE LEHMAN

Attesting Officer

*Commissioner of Patents and Trademarks*